United States Patent
Bakan et al.

(10) Patent No.: US 9,561,241 B1
(45) Date of Patent: Feb. 7, 2017

(54) GASTRORETENTIVE DOSAGE FORMS FOR MINOCYCLINE

(75) Inventors: Douglas A. Bakan, San Diego, CA (US); Waranush Jitpraphai, Chandler, AZ (US); Steven B. Newhard, Scottsdale, AZ (US); Mitchell S. Wortzman, Scottsdale, AZ (US)

(73) Assignee: Medicis Pharmaceutical Corporation, Bridgewater, NJ (US)

( * ) Notice: Subject to any disclaimer, the term of this patent is extended or adjusted under 35 U.S.C. 154(b) by 0 days.

(21) Appl. No.: 13/536,130

(22) Filed: Jun. 28, 2012

Related U.S. Application Data

(60) Provisional application No. 61/502,289, filed on Jun. 28, 2011, provisional application No. 61/508,573, filed on Jul. 15, 2011, provisional application No. 61/508,594, filed on Jul. 15, 2011, provisional application No. 61/508,352, filed on Jul. 15, 2011, provisional application No. 61/508,288, filed on Jul. 15, 2011, provisional application No. 61/508,582, filed on Jul. 15, 2011.

(51) Int. Cl.
| | |
|---|---|
| *A61K 9/48* | (2006.01) |
| *A61K 9/00* | (2006.01) |
| *A61K 9/20* | (2006.01) |
| *A01N 37/18* | (2006.01) |
| *A61K 31/65* | (2006.01) |

(52) U.S. Cl.
CPC ............ *A61K 31/65* (2013.01); *A61K 9/4858* (2013.01); *A61K 9/2054* (2013.01)

(58) Field of Classification Search
None
See application file for complete search history.

(56) References Cited

U.S. PATENT DOCUMENTS

| | | |
|---|---|---|
| 3,499,959 A | 3/1970 | Corn |
| 3,932,615 A | 1/1976 | Ito et al. |
| 3,957,980 A | 5/1976 | Noseworthy |
| 3,966,922 A | 6/1976 | Okamoto et al. |
| 4,086,332 A | 4/1978 | Armstrong |
| 4,126,680 A | 11/1978 | Armstrong |
| 4,138,475 A | 2/1979 | McAinsh et al. |
| 4,369,172 A | 1/1983 | Schor et al. |
| 4,376,118 A | 3/1983 | Daher et al. |
| 4,443,442 A | 4/1984 | Skillern |
| 4,701,320 A | 10/1987 | Hasegawa et al. |
| 4,764,377 A | 8/1988 | Goodson |
| 4,792,448 A | 12/1988 | Ranade |
| 4,806,529 A | 2/1989 | Levy |
| 4,837,030 A | 6/1989 | Valorose, Jr. et al. |
| 4,925,833 A | 5/1990 | McNamara et al. |
| 4,935,411 A | 6/1990 | McNamara et al. |
| 4,935,412 A | 6/1990 | McNamara et al. |
| 4,960,913 A | 10/1990 | Szalay et al. |
| 5,007,790 A | 4/1991 | Shell |
| 5,009,895 A | 4/1991 | Lui |
| 5,122,519 A | 6/1992 | Ritter |
| 5,167,964 A * | 12/1992 | Muhammad ......... A61K 9/5078 424/440 |
| 5,188,836 A | 2/1993 | Muhammad et al. |
| 5,202,128 A | 4/1993 | Morella et al. |
| 5,209,978 A | 5/1993 | Kosaka et al. |
| 5,211,958 A | 5/1993 | Akkerboom et al. |
| 5,217,493 A | 6/1993 | Raad et al. |
| 5,225,916 A | 7/1993 | Kikugawa et al. |
| 5,230,895 A | 7/1993 | Czarnecki et al. |
| 5,262,173 A | 11/1993 | Sheth et al. |
| 5,277,916 A | 1/1994 | Dwyer et al. |
| 5,283,065 A | 2/1994 | Doyon et al. |
| 5,300,304 A | 4/1994 | Sheth et al. |
| 5,324,751 A | 6/1994 | DuRoss |
| 5,348,748 A | 9/1994 | Sheth et al. |
| 5,413,777 A | 5/1995 | Sheth et al. |
| 5,459,135 A | 10/1995 | Golub et al. |
| 5,518,730 A | 5/1996 | Fuisz |
| 5,554,654 A | 9/1996 | Yu et al. |
| 5,582,837 A | 12/1996 | Shell |
| 5,665,776 A | 9/1997 | Yu et al. |
| 5,674,539 A | 10/1997 | Tomas |
| 5,698,593 A | 12/1997 | Peck |
| 5,776,489 A | 7/1998 | Preston et al. |
| 5,780,049 A | 7/1998 | Deckner et al. |
| 5,783,212 A | 7/1998 | Fassihi et al. |
| 5,789,395 A | 8/1998 | Amin et al. |
| 5,800,836 A | 9/1998 | Morella et al. |

(Continued)

FOREIGN PATENT DOCUMENTS

| | | |
|---|---|---|
| CA | 2025703 | 9/1990 |
| CA | 2068366 | 11/1992 |

(Continued)

OTHER PUBLICATIONS

A Comparison of the Side Effects Produced by Vectrin and Dynacin After Normal Dosage. Clinical Acne Reviews, vol. 2 Oct. 1977.
Agwuh, K.N., et al., "Pharmacokinetics of the tetracyclines including glycylcyclines," J. Antimicrobial Chemotherapy vol. 58, 256-265 (Jul. 1, 2006).
Akamatsu, et al., "Effect of Doxycycline on the Generation of Reactive Oxygen Species: A Possible Mechanism of Action of Acne Therapy with Doxycycline"; Acta Derm Venereol (Stockh), 1992; 72:178-179.
Akamatsu, et al., "Effects of subminimal inhibitory concentrations of minocycline on neutrophil chemotactic factor production in comedonal bacteria, neutrophil phagocytosis and oxygen metabolism", Archives of Dermatological Research, vol. 283, 1991, pp. 524-528.
American Hospital Formulary Service Drug Information 88, 1988, pp. 330-331.
American Hospital Formulary Service, AHFS Drug Information 446-448 (2003).

(Continued)

*Primary Examiner* — Jianfeng Song
(74) *Attorney, Agent, or Firm* — Andrew J. Anderson, Esq.; John E. Thomas, Esq.; Harter Secrest & Emery LLP

(57) ABSTRACT

The present disclosure relates to dosage forms and methods that enhance the absorption of minocycline in the gastrointestinal tract and thereby enhance bioavailability of the minocycline, and further provides methods of using these dosage forms for the treatment of conditions such as acne.

10 Claims, No Drawings

(56) References Cited

U.S. PATENT DOCUMENTS

| | | |
|---|---|---|
| 5,814,331 A | 9/1998 | Holen |
| 5,824,343 A | 10/1998 | Ng et al. |
| 5,834,450 A | 11/1998 | Su |
| 5,855,904 A | 1/1999 | Chung et al. |
| 5,908,838 A | 6/1999 | Gans |
| 5,972,389 A | 10/1999 | Shell et al. |
| 6,015,804 A | 1/2000 | Golub et al. |
| 6,087,382 A | 7/2000 | Bonner, Jr. et al. |
| 6,120,803 A | 9/2000 | Wong et al. |
| 6,165,513 A | 12/2000 | Dansereau et al. |
| 6,165,999 A | 12/2000 | Vu |
| 6,194,000 B1 | 2/2001 | Smith et al. |
| 6,340,475 B2 | 1/2002 | Shell et al. |
| 6,340,476 B1 | 1/2002 | Midha et al. |
| 6,429,204 B1 | 8/2002 | Golub et al. |
| 6,455,583 B1 | 9/2002 | Pflugfelder et al. |
| 6,497,902 B1 | 12/2002 | Ma |
| 6,548,083 B1 * | 4/2003 | Wong et al. ............... 424/473 |
| 6,585,997 B2 | 7/2003 | Moro et al. |
| 6,638,922 B2 | 10/2003 | Ashley et al. |
| 6,667,060 B1 | 12/2003 | Vandecruys et al. |
| 6,673,367 B1 * | 1/2004 | Goldenheim et al. ........ 424/464 |
| 6,673,843 B2 | 1/2004 | Arbiser |
| 6,863,830 B1 | 3/2005 | Purdy et al. |
| 6,958,161 B2 | 10/2005 | Hayes et al. |
| 7,008,631 B2 | 3/2006 | Ashley |
| 7,063,862 B2 | 6/2006 | Lin et al. |
| 7,211,267 B2 | 5/2007 | Ashley |
| 7,541,347 B2 | 6/2009 | Wortzman et al. |
| 7,544,373 B2 | 6/2009 | Wortzman et al. |
| 7,790,705 B2 | 9/2010 | Wortzman et al. |
| 7,919,483 B2 | 4/2011 | Wortzman et al. |
| 7,976,870 B2 | 7/2011 | Berner et al. |
| 2002/0015731 A1 | 2/2002 | Appel et al. |
| 2002/0044968 A1 | 4/2002 | van Lengerich |
| 2003/0044446 A1 | 3/2003 | Moro et al. |
| 2003/0082120 A1 | 5/2003 | Milstein |
| 2003/0130240 A1 | 7/2003 | Ashley |
| 2003/0139380 A1 | 7/2003 | Ashley |
| 2003/0199480 A1 | 10/2003 | Hayes et al. |
| 2003/0229055 A1 | 12/2003 | Ashley |
| 2004/0002481 A1 | 1/2004 | Ashley et al. |
| 2004/0037789 A1 | 2/2004 | Moneuze et al. |
| 2004/0115261 A1 | 6/2004 | Ashley |
| 2004/0127471 A1 | 7/2004 | Reisberg |
| 2004/0185105 A1 | 9/2004 | Berner et al. |
| 2004/0228912 A1 | 11/2004 | Chang et al. |
| 2005/0136107 A1 | 6/2005 | Patel et al. |
| 2005/0148552 A1 | 7/2005 | Ryan et al. |
| 2006/0293290 A1 | 12/2006 | Wortzman et al. |
| 2007/0154547 A1 | 7/2007 | Flanner et al. |
| 2007/0254855 A1 | 11/2007 | Wortzman et al. |
| 2007/0259039 A1 | 11/2007 | Wortzman et al. |
| 2007/0270390 A1 | 11/2007 | Wortzman et al. |
| 2007/0275933 A1 | 11/2007 | Wortzman et al. |
| 2008/0070872 A1 | 3/2008 | Wortzman et al. |
| 2008/0161273 A1 | 7/2008 | Arsonnaud et al. |
| 2008/0241197 A1 | 10/2008 | Wortzman et al. |
| 2008/0241235 A1 | 10/2008 | Wortzman et al. |
| 2008/0241236 A1 * | 10/2008 | Wortzman et al. ............ 424/465 |
| 2008/0241241 A1 | 10/2008 | Wortzman et al. |
| 2008/0242641 A1 | 10/2008 | Wortzman et al. |
| 2008/0242642 A1 | 10/2008 | Wortzman et al. |
| 2008/0260824 A1 | 10/2008 | Nangia et al. |
| 2008/0268045 A1 * | 10/2008 | Dervieux et al. ............. 424/468 |
| 2008/0318910 A1 | 12/2008 | Desjardins et al. |
| 2010/0035846 A1 | 2/2010 | Wortzman et al. |
| 2010/0203120 A1 * | 8/2010 | Coulter ........... 424/452 |
| 2010/0215744 A1 | 8/2010 | Watt et al. |
| 2010/0330131 A1 | 12/2010 | Wortzman et al. |
| 2012/0002892 A1 | 1/2012 | Eichhorn et al. |
| 2012/0093892 A1 | 4/2012 | Wortzman et al. |

FOREIGN PATENT DOCUMENTS

| | | |
|---|---|---|
| CA | 2090561 | 2/1993 |
| CN | 101658501 A | 3/2010 |
| CN | 101822650 A | 9/2010 |
| CN | 101836961 A | 9/2010 |
| EP | 0184389 | 6/1986 |
| EP | 0418565 | 3/1991 |
| EP | 0558913 | 9/1992 |
| EP | 1411848 | * 10/2004 |
| GB | 2414668 | 12/2005 |
| GB | 2 420 708 A | 6/2006 |
| JP | 2001-278781 A | 10/2001 |
| JP | 2002-509887 A | 4/2002 |
| JP | 2004-224754 A | 8/2004 |
| WO | WO 93/18755 | 9/1993 |
| WO | WO 98/11879 | 3/1998 |
| WO | WO 98/55107 | 12/1998 |
| WO | WO 99/49868 A1 | 10/1999 |
| WO | WO 99/58131 | 11/1999 |
| WO | WO 02/080932 | 10/2002 |
| WO | WO 03/088906 | 10/2003 |
| WO | WO 2004/012700 | 2/2004 |
| WO | WO 2004/078111 A2 | 9/2004 |
| WO | WO 2004/091483 A2 | 10/2004 |
| WO | WO 2007/038867 A1 | 4/2007 |
| WO | WO 2007/102447 A1 | 9/2007 |
| WO | WO 2008/102161 A2 | 8/2008 |
| WO | WO 2010/033800 A2 | 3/2010 |
| WO | WO 2010/046932 A2 | 4/2010 |

OTHER PUBLICATIONS

Anlar, et al., "Physico-chemical and bioadhesive properties of polyacrylic acid polymers," Pharmazie 48(4):285-287, Abstract, Verlag Pharmazautischer Verlag, Germany (1993).

Arndt et al., "What disorders present with inflamed skin?" Cutaneous Medicine and Surgery, an Intergrated Program in Dermatology, vol. 1, pp. 470-471, 1996.

Arnold et al., Andrews' Diseases of the Skin: Clinical Dermatology, 8th Edition, p. 254, 1990.

Bikowski, "Treatment of Rosacea With Doxycycline Monohydrate", Therapeutics for the clinician, vol. 66, Aug. 2000, pp. 149-152.

Brown, et al., "Diagnosis and Treatment of Ocular Rosacea", Official Journal of American Academy of Ophthalmology, vol. 85, Aug. 1978, pp. 779-786.

Cartwright, A.C., et al., "A comparison of the bioavailability of minocycline capsules and film-coated tablets," J. Antimicrobial Chemotherapy vol. 1, 317:322 (1975).

Champion et al., "Disorders of the Sebaceous Glands," Textbook of Dermatology, 6th Edition, vol. 3, pp. 1958-1961, 1998.

Cohen, P.M., "A General Practice Study Investigating the Effect of Minocin 50 mg b.d. for 12 Weeks in the Treatment of Acne Vulgaris," J. Int. Med. Res. 13:214-221, Cambridge Medical Publications, England (1985).

Coskey, R.J., "Acne: Treatment with Minocycline," Therapeutics for the Clinician 17:799-801, Cutis, United States (1976).

Cullen, S.I., "Low-Dose Minocycline Therapy in Tetracycline-Recalcitrant Acne Vulgaris," Therapeutics for the Clinician 21:101-105, Cutis, United States (1978).

Cullen, S.I., et al., "Minocycline therapy in acne vulgaris", Cutis vol. 17, No. 6, 1208-1214 (1976).

Darrah, et al., "An open multicentre study to compare fusidic acid lotion and oral minocycline in the treatment of mild-to-moderate acne vulgaris of the face", European Journal of Clinical Research, 1996, vol. 8, pp. 97-107.

Del Rosso, et al., "Current Approach to Acne Management: A Community-Based Analysis," Cutaneous Medicine for the Practitioner 83(6S):5-24, Quadrant HealthCom, United States (2009).

Del Rosso, et al., "Optimizing Use of Oral Antibiotics in Acne Vulgaris," Dermatologic. clinics. 27: 33-42, Elsevier Health Sciences Division, United States (2009).

(56) References Cited

OTHER PUBLICATIONS

Del Rosso, J.Q., "A status report on the use of subantimicrobial-dose doxycycline: a review of the biologic and antimicrobial effects of the tetracyclines," Cutis 118-122 (Jun. 1, 2004).

Del Rosso, J.Q., "What's new in the Medicine Cabinet?", Supplement to the Feb. 2005 Skin and Aging Conference, pp. 3-6.

Del Rosso, J.Q., "Clinical Significance of Brand Versus Generic Formulations: Focus on Oral Minocycline," Cutis, vol. 77, 153-156, Mar. 2006.

Del Rosso, J.Q., et al. "Weight-based Dosing of a Novel Antibiotic for Moderate-to-Severe Acne Vulgaris Offers Potential for Improved Safety and Tolerability," www.millennium.com/go/acne, Millennium CME Institute, Inc., 2006.

Del Rosso, et al., "Recently Approved Systemic Therapies for Acne Vulgaris and Rosacea," Drug Therapy Topics, vol. 80, Aug. 2007, p. 113-120.

DePaz, S., et al., "Severe hypersensitivity reaction to minocycline", Invest. Allergol. Clin. Immunol., vol. 9, No. 6, 403-404 (1999).

Dreno, et al., "Multicenter Randomized Comparative Double-Blind Controlled Clinical Trial of the Safety and Efficacy of Zinc Gluconate versus Minocyclin Hydrochloride in the Treatment of Inflammatory Acne vulgaris", Dermatology, 2001, vol. 203, pp. 135-140.

Drugs.com, Drug information online, Minocin PAC product information, Aug. 2007.

Eady, A.E., et al., "Is antibiotic resistance in cutaneous propionibacteria clinically relevant?", Amer. J. Clin. Dermatol., vol. 4, No. 12, 813-831 (2003).

Elkayam, O., et al., "Minocycline-Induced Autoimmune Syndromes: An Overview," Seminars in Arthritis and Rheumatism 28(6):392-397, Stratton, United States (1999).

Fanning, et al., "Distressing Side-Effects of Minocycline Hydrochloride," Arch. Intern. Med., vol. 136, pp. 761-762 (1976).

Fernandez-Obregon, A.C., "Azithromycin for the treatment of acne," International Journal of Dermatology 2000, 39, 45-50.

Fingleton, B., "CMT-3 CollaGenex," Current Opinion in Investigational Drugs, vol. 4, No. 12, 1460-1467, Dec. 2003.

Fleischer, A.B. et al. "Safety and Efficacy of a New Extended-Release Formulation of Minocycline." Cutis 2006; 78 (suppl 4):21-31.

Freedberg, et al., "Fizpatrick's Dermatology in General Medicine," 5th Edition, vol. 1, pp. 77-78, 1999.

Freeman, et al., "Therapeutic Focus Minocycline in the treatment of acne", BJCP, Mar. 1989, vol. 43, pp. 112-114.

Gans et al. The Solubility and Complexing properties of Oxytetracycline and Tetracycline II, Journal of the American Pharmaceutical Association, Sci. Ed. 46, No. 10, Oct. 1957.

Gao, P., et al., "Swelling of Hydroxypropyl Methylcelluose Matrix Tablets. 2. Mechanistic Study of the Influence of Formulation Variables on Matrix Performance and Drug Release," Journal of Pharmaceutical Sciences 85(7):732-740, American Chemical Society and American Pharmaccutical Association, United States (1996).

Gardner, K.J., et al., Comparison of serum antibiotic levels in acne patients receiving the standard or a modified release formulation of minocycline hydrochloride. Clinical and Experimental Dermatology, vol. 22 pp. 72-76, Jan. 1997.

Garner SE, et al., "Minocycline for acne vulgaris: efficacy and safety", (Cochrane Review), The Cochrane Library, issue 1, 2004, Chichester, UK: John Wiley & Sons, Ltd.

Goldstein, N.S., et al., "Minocycline as a cause of drug-induced autoimmune hepatitis", Amer. J. Clin. Pathol., vol. 114, 591-598 (2000).

Gollnick, Harald, et al., "Management of Acne, a Report From a Global Alliance to Improve Outcomes in Acne", Supplement to Journal of the American Academy of Dermatology, Jul. 2003, vol. 49, No. 1, S1-38.

Golub, et al., "Tetracyclines Inhibit Connective Tissue Breakdown: New Therapeutic Implications for an Old Family of Drugs", Critical Reviews in Oral Biology and Medicine, vol. 2, No. 2, 1991, pp. 297-322.

Gould, et al., "Minocycline Therapy," Arch. Otolaryngol., vol. 96, p. 291 (1972).

Greco, T.P., et al., "Minocycline Toxicity: Experience with an Altered Dosage Regimen," Current Therapeutic Research 25(2):193, Therapeutic Research Press, Inc., United States (1979).

Gump, D.W., et al., "Side effects of minocycline: different dosage regimens," Antimicrobial Agents and Chemotherapy, vol. 12, No. 5, 642-646 (Nov. 1977).

Gupta, A.K., et al., Solodyn (Minocycline HCI, USP) Extended-Release Tablets, LE JACQ, 291-292, Nov. Dec. 2006.

Harrison, "A comparison of doxycycline and minocycline in the treatment of acne vulgaris", Clinical and Experimental Dermatology, 1998, vol. 13, pp. 242-244.

Healy, N., et al., "Fortnightly Review: Acne Vulgaris," BMJ vol. 308, 831-833 (1994).

Hersle, et al., "Minocycline in Acne Vulgaris: a Double-Blind Study", Current Therapeutic Research, Mar. 1976, vol. 19, No. 3, pp. 339-342.

Hubbell, C.G., et al. Efficacy of Minocycline Compared with Tetracycline in Treatment of Acne Vulgaris, Archives of Dermatology, vol. 118, pp. 989-992, Dec. 1982.

Illig, "Positive Side Effects of Antibiotic and Antimicrobial Substances in Therapy", Infection, vol. 7, Suppl. 6, 1979, pp. S 584-588.

Is minocycline overused in acne?, Drug and Therapeutics Bulletin. vol. 44 No. 8, 60-62, Aug. 2006.

Islam, M.M., A Nonantibiotic Chemically Modified Tetracycline (CMT-3) Inhibits intimal Thickening, American Journal of Pathology; vol. 163, No. 4, 1557-1566, Oct. 2003.

Johnson, B.A., et al., "Use of systemic agents in the treatment of acne vulgaris," Am. Fam Physician vol. 62, 1823-1830, 1835-1836 (Oct. 15, 2000).

Jonas, et al., "Minocycline", Therapeutic Drug Monitoring, vol. 4, 1982, pp. 137-145.

Kelly, et al., "Metabolism and Tissue Distribution of Radiosotopically Labeled Minocycline", Elsevier Toxicology and Applied Pharmacology, 1967, vol. 11, pp. 171-183.

Lawrenson, R.A., et al., "Liver damage associated with minocycline use in acne", Drug Safety, vol. 23, No. 4, 333-349 (2000).

Leyden, et al. 2006. New Extended-Release Minocycline. First Systemic Antibiotic Approved for the Treatment of Acne. A Supplement to Cutis, 78(4S): 1-32.

Leyden, J. Introduction. Cutis 2006; 78 (suppl 4):4-5.

Leyden, James J., "Absorption of minocycline hydrochloride and tetracycline hydrochloride", J. Am. Acad. Dermatol. 12:308-312, 1985.

Leyden, James J., et al., "Clinical Considerations in the Treatment of Acne Vulgaris and Other Inflammatory Skin Disorders: Focus on Antibiotic Resistance", Cutis 2007 (suppl. 6), vol. 79, No. 65, 9-25.

Leyden, James J., et al., "Comparison of Tazarotene and Minocycline Maintenance Therapies in Acne Vulgaris", Archives of Dermatology, May 2006, 605-612.

Leyden, James J., et al., "Pseudomonas aeruginosa Gram-Negative Folliculitis", Archives of Dermatology, 1979, vol. 115, 1203-1204.

Leyden, James J., et al., "Tetracycline and Minocycline Treatment, Effects on Skin-Surface Lipid Levels and Propionibacterium acnes", Archives of Dermatology, 1982, vol. 118, 19-22.

Leyden, James J., et al., "The antimicrobial effects in vivo of minocycline, doxycycline and tetracycline in humans", The Journal of Dermatological Treatment, Dec. 1996, vol. 7, No. 4, 223-225.

Li, J., et al., Evidence for Dissolution Rate-Limited Absorption of COL-3, a Matrix Metalloproteinase Inhibitor, Leading to the Irregular Absorption Profile in Rats after Oral Administration, Pharmaceutical Research, Vo. 19, No. 11, 1655-1662, Nov. 2002.

Lokeshwar, B.L., et al., Inhibition of Cell Proliferation, Invasion, Tumor Growth and Metastasis by an Oral Non-Antimicrobial Tetracycline Analog (COL-3) in a Metastatic Prostate Cancer Model, International Journal of Cancer: 98, 297-309 (2002).

MacDonald, H., et al., "Pharmacokinetic studies on minocycline in man," American Cyanamid (Lederle Laboratories division) 852-861 (1973).

Mahaguna "Influence of hydroxypropyl methylcellulose polymer on in vitro and in vivo performance of controlled release tablets

(56) References Cited

OTHER PUBLICATIONS containing alprazolam," European Journal of Pharmaceutics and Biopharmaceutics, vol. 56, pp. 461-468, (2003).

Marks, Ronald, et al., (eds.) "Dermatologic Therapy in Current Practice", Chapter 3, 35-44 (2002).

Millar, MB, ChB, et al., "A general practice study investigating the effect of minocycline (Minocin) 50 mg bd for 12 weeks in the treatment of acne vulgaris", British Journal of Clinical Practice, vol. 41, No. 8, Aug. 1987, pp. 882-886.

Minocin Product Insert, Wyeth Pharmaceuticals Inc. Rev 10/05.

Nayak, et al., "Gastroretentive drug delivery systems: a review," Asian Journal of Pharmaceutical and Clinical Research, 3(1):2-10, Elsevier, United States (2010).

Ochsendorf, F., Systemic antibiotic therapy of acne vulgaris, Journal der Deutschen Dermatologischen Gesellschaft, 4:828-841, 2006.

Opadry II Brochure, 1990, 3 pages.

Physician's Desk Reference; Minocin®: Minocycline Hydrochloride for Oral Use; Physician's Desk Reference, 1989, pp. 1134-1136, 43rd Edition; Edward R. Barnhard, publisher, Medical Economics Co. Inc.; Oradell, NJ.

Physician's Desk Reference®, 51st Ed., Minocin® Minocycline Hydrochloride Pellet-Filled Capsules, Thomson PDR, Montvale, New Jersey, pp. 1429-1431 (1997).

The 2002 Physician's Desk Reference, 56th Ed., Minocin®, Minocycline Hydrochloride Pellet-Filled Capsules, Thomson PDR, Montvale, New Jersey, pp. 1864-1865 (2002).

Piérard-Franchimont, et al. 2002. Lymecycline and Minocycline in Inflammatory Acne. Skin Pharmacol Appl Skin Physiol, 15:112-119.

Plott, G., Extended-Release Minocycline: Is Efficacy Dose-dependent in the Approved Dose Range?, Poster Presentation for the DUSA Pharmaceuticals, Inc. Medical Conferences and Trade Shows, Hawaii, Mar. 3-9, 2007.

Plott, R. T. and Wortzman, M. Key Bioavailability Features of a New Extended-Release Formulation of Minocycline Hydrochloride Tablets. Cutis 2006; 78 (suppl 4):6-10.

Prescribingreference.com, Prescribing Reference, Drug News—Minocin PAC for Acne (Oct. 11, 2006).

Samani, S. M., et al., "The effect of polymer blends on release profiles of diclofenac sodium from matrices," European Journal of Pharmaceuticals and Biopharmaceuticals 55(3):351-355, Elsevier Science B.V., Netherlands (2003).

Sapadin, A.N., et al., Tetracyclines: Nonantibiotic properties and their clinical implications, American Academy of Dermatology, Inc., 258-265, Feb. 2006.

Seftor, R.E.B., et al., Chemically modified tetracyclines inhibit human melanoma cell invasion and metatasis, Clinical & Experimental Metastasis, vol. 16, No. 3, 217-225 (1998).

Shah, et al., "In vitro Dissolution Profile Comparison—Statistics and Analysis of the Similarity Factor, f2," Pharmaceutical Research, vol. 15, No. 6, pp. 889-896 (1998).

Shalita, A., "The integral role of topical and oral retinoids in the early treatment of acne," J. European Acad. Derm. Venereol. vol. 15, Suppl. 3, 43-49 (2001).

Sheehan-Dare, et al "A Double-blind Comparison of Topical Clindamycin and Oral Minocycline in the Treatment of Acne Vulgaris", Acta Derm Venereol (Stockh), 70, pp. 534-537, 1990.

Smit, "Minocycline versus Doxycycline in the Treatment of Acne vulgaris", Dermatologica, vol. 157, 1978, pp. 186-190.

Smith, Kelly, et al., "Safety of Doxycycline and Minocycline: A Systematic Review", Clinical Therapeutics, The International Peer-Reviewed Journal of Drug Therapy, vol. 27, No. 9, Sep. 2005, 1329-1342.

Solodyn (Minocycline HCI Extended Release Tablets) Labeling and package insert information, submitted with a New Drug Application approved May 8, 2006.

Stewart, D.M. et al. Dose Ranging Efficacy of New Once-Daily Extended-Release Minocycline for Acne Vulgaris. Cutis 2006; 78 (suppl4):11-20.

Ta et al., Effects of Minocycline on the Ocular Flora of Patients with Acne Rosacea or Seborrheic Blepharitis, Cornea vol. 22(6): 545-548, 2003.

Torok, et al., "Long-Term Safety of a Modified-Release Formulation of Minocycline for Treating Moderate to Severe Acne," program and abstracts of the Foundation of Research and Education in Dermatology Winter Clinical Dermatology Conference; Mar. 14-18, 2008, Kapalua, Hawaii, 9 pages.

Unites States Pharmacopeia: Dissolution test described in US Pharmacopoeia XXIII, <724> Drug Release: Extended-release Articles-General Drug Release Standard, USP 23:1793-1799, USP, United States (1995).

Von Wittenau, S., et al., "The Distribution of Tetracyclines in Tissues of Dogs After Repeated Oral Administration", The Journal of Pharmacology and Experimental Therapeutics, 1965, vol. 152, No. 1, pp. 164-169.

Webster, "Inflammation in acne vulgaris", Journal of the American Academy of Dermatology, vol. 33, No. 2, part 1, Aug. 1995, pp. 247-253.

Webster, et al., "Suppression of Polymorphonuclear Leukocyte Chemotactic Factor Production in Propionibacterium acnes by Subminimal Inhibitory Concentrations of Tetracycline, Ampicillin, Minocycline, and Erythromycin", Antimicrobial Agents and Chemotherapy vol. 21, No. 5, May 1982, pp. 770-772.

Williams D.N., et al., Minocycline: Possible vestibular side-effects. Lancet. Sep. 28, 1974;2(7883):744-6.

Yang, Jian, et al., LinNan kin Disease Magazine, No. 1, p. 38 (1994).

"Bioadhesion," Lubrizol Pharmaceutical Bulletin 23:1-20, Edition: Oct. 29, 2008, The Lubrizol Corporation, United States (2008).

"Carbopol and its Applications in pharmaceutical dosage forms," accessed at www.pharmainfo.net, submitted Oct. 27, 2007, 6 pages.

"Carbopol Polymers for Pharmaceutical Drug Delivery Applications," accessed at http://www.drugdeliverytech.com/Main/Back-Issues/345.aspx, available online Sep. 27, 2008, 3 pages.

International Search Report and Written Opinion dated Feb. 26, 2007, for PCT/US06/23761.

International Search Report and Written Opinion mailed Dec. 5, 2007, for PCT/US2007/008086, pp. 1-18.

International Preliminary Report on Patentability for International Application No. PCT/US2007/008086, United States Patent Office, United States, mailed on Feb. 2, 2011.

International Search Report and Written Opinion for International Application No. PCT/US2009/052873, United States Patent Office, United States, mailed Oct. 1, 2009.

International Preliminary Report on Patentability for International Application No. PCT/US2009/052873, United States Patent Office, United States, mailed Oct. 4, 2010.

Extended European Search Report in European Application No. 06773507.6, dated Jul. 1, 2009.

Examination Report in NZ Application No. 564093, dated Oct. 29, 2009.

Office Communication dated Nov. 6, 2009 in Chinese Pat. App. Ser. No. 2006800224203.

Office Action mailed Nov. 6, 2007, in U.S. Appl. No. 11/166,817, inventors Wortzman et al., filed Jun. 24, 2005.

Office Action mailed Nov. 13, 2008, in U.S. Appl. No. 11/166,817, inventors Wortzman et al., filed Jun. 24, 2005.

Office Communication dated Nov. 6, 2007 in U.S. Appl. No. 11/776,669.

Office Communication dated Jun. 17, 2008 in U.S. Appl. No. 11/776,669.

Office Communication dated Dec. 1, 2008 in U.S. Appl. No. 11/776,669.

Office Communication dated Jun. 25, 2009 in U.S. Appl. No. 11/776,669.

Office Communication dated Mar. 31, 2010 in U.S. Appl. No. 11/776,669.

Office Communication dated Nov. 6, 2007 in U.S. Appl. No. 11/776,676.

Office Communication dated Aug. 8, 2008 in U.S. Appl. No. 11/776,676.

(56) References Cited

OTHER PUBLICATIONS

Office Communication dated Jun. 10, 2009 in U.S. Appl. No. 11/776,676.
Office Communication dated Mar. 31, 2010 in U.S. Appl. No. 11/776,676.
Office Communication dated Nov. 6, 2007 in U.S. Appl. No. 11/776,711.
Office Communication dated Jun. 17, 2008 in U.S. Appl. No. 11/776,711.
Office Communication date May 29, 2009 in U.S. Appl. No. 11/776,711.
Office Communication dated Mar. 31, 2010 in U.S. Appl. No. 11/776,711.
Office Communication dated Nov. 17, 2008 in U.S. Appl. No. 11/944,186.
Office Communication date May 29, 2009 in U.S. Appl. No. 11/944,186.
Office Communication dated Apr. 2, 2010 in U.S. Appl. No. 11/944,186.
Office Communication dated Dec. 24, 2008 in U.S. Appl. No. 11/695,514.
Office Communication dated Jun. 10, 2009 in U.S. Appl. No. 11/695,514.
Office Communication dated Jul. 23, 2008 in U.S. Appl. No. 11/695,539.
Office Communication dated Dec. 23, 2008 in U.S. Appl. No. 11/695,539.
Office Action mailed Jul. 23, 2008, in U.S. Appl. No. 11/695,539, inventors Wortzman et al., filed Apr. 2, 2007.
Office Communication dated Jul. 22, 2008 in U.S. Appl. No. 11/695,528.
Office Action mailed Jul. 22, 2008, in U.S. Appl. No. 11/695,528, inventors Wortzman et al., filed Apr. 2, 2007.
Office Action mailed Nov. 17, 2009, in U.S. Appl. No. 12/253,845, inventors Wortzman et al., filed Oct. 17, 2008.
Office Action mailed Mar. 4, 2010, in U.S. Appl. No. 12/253,845, inventors Wortzman et al., filed Oct. 17, 2008.
Office Action mailed Aug. 4, 2010, in U.S. Appl. No. 12/253,845, inventors Wortzman et al., filed Oct. 17, 2008.
Office Action mailed Mar. 7, 2011, in U.S. Appl. No. 11/695,513, inventors Wortzman et al., filed Apr. 2, 2007.
Office Action mailed Oct. 25, 2011, in U.S. Appl. No. 11/695,513, inventors Wortzman et al., filed Apr. 2, 2007.
Office Action mailed Oct. 18, 2011, in U.S. Appl. No. 12/536,359, inventors Wortzman et al., filed Aug. 5, 2009.
Office Action mailed Jun. 1, 2012, in U.S. Appl. No. 12/536,359, inventors Wortzman et al., filed Aug. 5, 2009.
Office Action mailed May 24, 2011, in U.S. Appl. No. 12/875,876, inventors Wortzman et al., filed Sep. 3, 2010.
Office Action mailed Dec. 10, 2012, in U.S. Appl. No. 12/756,962, inventors Watt et al., filed Apr. 8, 2010.
Office Action mailed Mar. 7, 2013, in U.S. Appl. No. 12/861,424, inventors Wortzman et al., filed Aug. 23, 2010.
Office Action mailed Aug. 19, 2013, in U.S. Appl. No. 12/861,424, inventors Wortzman et al., filed Aug. 23, 2010.
English Language Abstract of Japanese Publication No. JP402006437A, published Jan. 10, 1990.
U.S. Appl. No. 61/235,898, inventors Wortzman, M., et al., filed Aug. 21, 2009.
U.S. Appl. No. 61/210,882, inventors Wortzman, M., et al., filed Mar. 23, 2009.
U.S. Appl. No. 61/086,728, inventors Wortzman, M., et al., filed Aug. 6, 2008.

* cited by examiner

GASTRORETENTIVE DOSAGE FORMS FOR MINOCYCLINE

RELATED APPLICATIONS

This application claims priority to U.S. Provisional Application No. 61/502,289, filed Jun. 28, 2011, U.S. Provisional Application No. 61/508,573, filed Jul. 15, 2011, U.S. Provisional Application No. 61/508,594, filed Jul. 15, 2011, U.S. Provisional Application No. 61/508,352, filed Jul. 15, 2011, U.S. Provisional Application No. 61/508,288, filed Jul. 15, 2011, and U.S. Provisional Application No. 61/508,582, filed Jul. 15, 2011; all of which are incorporated herein by reference in their entireties.

BACKGROUND

Minocycline, when administered in currently available dosage forms has various side effects. These side effects include those affecting the gastrointestinal tract, such as reflux, and vestibular side effects or symptoms such as vertigo, dizziness, ear and labyrinth disorders, and nausea. It would therefore be desirable to develop a dosage form that regulates the delivery and/or absorption of minocycline so that the incidence of side effects in human patients is reduced or eliminated without compromising therapeutic efficacy.

SUMMARY

The present disclosure relates to methods and dosage forms for enhancing the absorption of minocycline in the gastrointestinal tract to thereby enhance bioavailability of the minocycline. More particularly, the present disclosure relates to oral dosage forms of minocycline that control the spatial and temporal delivery of minocycline in the gastrointestinal tract. This controlled spatial and temporal delivery provides a site and rate of release, respectively, of the minocycline into the gastrointestinal tract that enhances the amount of the minocycline absorbed into the bloodstream, thereby enhancing bioavailability of the minocycline and concomitantly reducing the quantity of minocycline required to be administered to a patient.

In certain embodiments, the present disclosure provides dosage forms and methods of administration that enhances the absorption of minocycline in the gastrointestinal tract.

In other embodiments, the present disclosure further provides dosage forms and methods of administration that enhance bioavailability of the minocycline.

In other embodiments, the present disclosure provides a spatial and temporal delivery of minocycline in the gastrointestinal tract resulting in improved bioavailability and absorption of the minocycline into the bloodstream. In some embodiments, the improved bioavailability after a single dose administration is at least about 50% greater relative to the bioavailability of immediate release formulations.

In some embodiments, the present disclosure provides improved bioavailability of minocycline, yet side effects, particularly gastrointestinal side effects, such as reflux, and/or vestibular side effects or symptoms such as vertigo, dizziness, ear and labyrinth disorders, and nauseaare reduced or minimized. In particular, the improved bioavailability can be achieved while maintaining therapeutic efficacy with an otherwise reduced amount of minocycline administered to the patient while still minimizing or reducing side effects, particularly gastrointestinal and/or vestibular side effects in comparison to immediate release forms of minocycline.

In some embodiments, the dosage form configured such that when administered, there are reduced or minimized vestibular side effects or symptoms such as dizziness, ear and labyrinth disorders, nausea, and vertigo. When stating that side effects are reduced or minimized, it is meant that the number (incidence) and/or the severity of the side effects are reduced or minimized. Minimization should result in the dosage form having little or substantially no side effects or a diminution and possible elimination of side effects.

In some embodiments, the spatial delivery of the minocycline is targeted to one or more specific areas of the gastrointestinal tract, for example, the stomach, the duodenum, or a combination thereof. The present disclosure also provides that the temporal delivery of the minocycline controls the rate and manner of release of the minocycline into the desired, specific area. When desired, the temporal delivery can be metered and can also be targeted to commence release at a specific period of time after administration and sustain release in the desired specific area, e.g., for as long as possible. For example, when the desired spatial area is the stomach and duodenum, the temporal delivery can commence preferably within from 2.5 to 5 hours, after administration to the patient. If the spatial area is only the stomach, the release of the minocycline can occur within about 2.5 to about 5 hours after administration. If the spatial area is only the duodenum, the release can occur within 2 hours after arrival in the duodenum.

The dosage form preferably exhibits high levels of bioavailability, while maintaining control of or reducing side effects, particularly vestibular side effects or symptoms such as vertigo, dizziness or blurred vision as compared to immediate release formulations of minocycline.

For example, as compared to SOLODYN®, the dosage form of the present disclosure has a relative bioavailability of at least 20%, and preferably at least 30% at the outset. After steady-state is reached in seven days, SOLODYN® has a relative bioavailability of 70% when compared to an immediate release dosage form of minocycline. Thus, the dosage forms of the present invention have a relative bioavailability as compared to immediate-release dosage forms (e.g., MINOCIN®) of at least about 84%.

In certain embodiments, the dosage form has improved bioavailability that is defined as a bioavailability that is at least about 50% relative to an immediate release minocycline, yet maintains or reduces side effects, particularly gastrointestinal side effects. The improved bioavailability can be at least about 50%, at least about 70%, at least about 80%, at least about 90%, or at least about 91% relative to the bioavailability of an immediate release dosage form such as MINOCIN®. In certain embodiments, the bioavailability of the minocycline in the dosage forms described herein can be an absolute bioavailability of at least about 50%, at least about 70%, at least about 80%, at least about 85%, at least about 90%, and in some embodiments, at least about 95% of the minocycline dosed. Bioavailability is determined via methods known in the art using conventional measures, such as AUC and dose.

The present disclosure further provides embodiments in which about 60 wt % to about 80 wt % of the minocycline is released in the stomach and about 40 wt % to about 20 wt % of the minocycline is released in the duodenum. In other embodiments, about 20 wt % to about 40 wt % of the minocycline is released in the stomach and about 80 wt % to about 60 wt % of the minocycline is released in the duodenum. In some embodiments, the minocycline release in the stomach and duodenum takes place at ratios of about 70% stomach to about 30% duodenum, or about 30% stomach to about 70% duodenum, by weight. In other embodiments, the release ratios between the stomach and duodenum can be adjusted slightly to maximize bioavailability, minimize adverse events, reduce the administered dose, and address any reflux reaction that normally accompanies ingestion of minocycline.

The present disclosure still further provides that Tmax and Cmax are at appropriate levels such that gastrointestinal and vestibular side effects are substantially diminished or eliminated. The minocycline plasma concentration vs. time profile can be a relatively flat profile and thereby provide a substantially constant AUC value The minocycline oral dosage forms may be floatable, swellable, bioadhesive, osmotic or any combination thereof and have an immediate or delayed or extended or pulsatile release or any combinations of such releases.

Further according to the present disclosure, there is provided a method of treating acne in a patient comprising a step of administering any one of the osmotic oral dosage forms of the present disclosure to the patient once per day.

DETAILED DESCRIPTION

As stated above, the present disclosure provides dosage forms and methods of administration that enhance the absorption of minocycline in the gastrointestinal tract. The enhanced absorption achieves enhanced bioavailability of the minocycline in the patient. The dosage forms and methods of the present disclosure, provide for a focused spatial and temporal delivery of minocycline in the gastrointestinal tract, which improves bioavailability and absorption of the minocycline into the bloodstream.

As used in the present disclosure, the term "minocycline" includes minocycline free base and pharmaceutically acceptable salts and derivatives thereof, including but not limited to esters. Useful forms of minocycline for the present disclosure include, but are not limited to, minocycline base, minocycline maleate, minocycline mesylate, minocycline hydrochloride and minocycline citrate. In certain embodiments, minocycline hydrochloride is preferred.

In all embodiments of the present disclosure, the Tmax and the maximum plasma concentration (Cmax) of minocycline that is produced by the dosage forms are at appropriate levels so that gastrointestinal and vestibular side effects are substantially diminished or eliminated. It is believed that a more constant pharmacokinetic profile, ADME/PK, providing a stable plasma concentration of minocycline over a sustained period of time will result in an improved drug exposure profile (as measured by the area under the concentration vs. time curve (AUC) profile) that will allow lower overall dosing so that side effects are reduced or minimized without compromising therapeutic efficacy. Significantly, the amount of the minocycline needed to effect therapeutic treatment of acne using the dosage forms described herein is less than prior minocycline products used to treat acne.

In certain embodiments, the amount of minocycline can be administered based on the body weight of the person or patient. Specifically, the amount of minocycline can be administered once daily and be between about 0.6 to about 1.8 mg/kg, between about 0.9 mg/kg to about 1.5 mg/kg, between about 1.0 mg/kg to about 1.3 mg/kg, and in other embodiments about 1.2 mg/kg, based on the body weight of the patient. The body weight of the patient can be determined by conventional means, such as simply weighing the patient on a scale. The dosage form can then be calculated to provide about, e.g., 1.2 mg/kg/day.

The dosage form preferably exhibits high levels of bioavailability in human patients yet maintains control of or reduces side effects, as well as substantially maintain therapeutic efficacy. In certain embodiments, the percent relative bioavailability of the minocycline in the dosage form is at least 50%, at least about 75%, at least about 80%-85%, or at least about 90% relative to the bioavailability of immediate release minocycline. Relative bioavailability is determined via methods known in the art using conventional measures, such as AUC and dose. As stated, the improved bioavailability is achieved with a reduction of the amount of the minocycline that would otherwise be needed to achieve a given therapeutic effect.

Because of the increased bioavailability of the dosage forms described herein, less minocycline is needed to achieve a desired pharmaceutical effect. As such the dosage forms described herein can comprise about 90% or less, about 80% or less, about 70% or less, about 60% or less, or about 50% or less minocycline as compared to the amount contained in an immediate release form, yet still be effective.

The physical retention and controlled temporal release of the minocycline from an oral dosage form in desired spatial areas, such as the stomach or the duodenal portion of the small intestine, or a combination of both, provides the enhanced bioavailability, and thus sustainability, of the active agent in the person or patient. In some cases, the duodenal portion of the small intestine, and not the entire small intestine, is the desired area of retention outside of the stomach because minocycline is in its most lipophilic form and is most stable at the pH found in the duodenum. Lipophilicity promotes absorption across the gut wall. Because sustaining the presence of minocycline in the duodenum may be difficult, some embodiments described herein provide for delivery and absorption in the stomach. Absorption in the stomach can be achieved for a much longer duration than in the duodenum, yet the active ingredient can pass to the duodenum over time.

Significantly, the temporal delivery of the minocycline controls the rate, duration and manner of release of the minocycline into the desired, specific area. Preferably, the temporal delivery should be metered. Also, it should be precisely targeted to commence release at a specific period of time after administration and maintain release for as long as possible in the desired, specific area. In embodiments in which the minocycline release is in the stomach, it is desired that the release commence at about 2.5 hours, and continue between about 2.5 hours and about 5 hours after administration to the patient. In embodiments in which there is release in the duodenum, whether in part or entirely, the release in the duodenum can occur within 2 hours upon arrival in the duodenum. Whether release is desired either entirely in the stomach or the duodenum, preferably, greater than 90 wt % of the minocycline is released in the desired area. In some embodiments wherein the minocycline is released in both the stomach and the duodenum, the amount released in each will be controlled. For example, in some embodiments, about 60 wt % to about 80 wt % of the minocycline is released in the stomach and about 40 wt % to about 20 wt % of the minocycline is released in the duodenum. In other embodiments, about 20 wt % to about 40 wt % of the minocycline is released in the stomach and about 80 wt % to about 60 wt % of the minocycline is released in the duodenum. In some embodiments, it is preferable that the minocycline release in the stomach and duodenum takes place at ratios of about 70% stomach to about 30% duodenum; or about 30% stomach to about 70% duodenum, by weight.

In other embodiments, the release ratios between the stomach and duodenum can be adjusted slightly to maximize bioavailability, minimize adverse events, reduce the administered dose, and address any reflux reaction that normally accompanies ingestion of minocycline. For example, the release ratios between the stomach and small intestine or between the small intestine and the stomach can be about 1:1, about 1:1.25, about 1:1.5, about 1:1.75, about 1:2, about 1:2.25, about 1:2.5, about 1:2.75, about 1:3, about 1:3.5, about 1:4, about 1:4.5, about 1:5, about 1:5.5 about 1:6, about 1:6.5, about 1:7, about 1:7.5, about 1:8, about 1:8.5, about 1:9, about 1:9.5, about 1:10, about 1.25:1, about 1.5:1, about 1.75:1, about 2:1, about 2.25:1, about 2.5:1, about 2.75:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, or about 10:1.

To achieve the desired spatial and temporal effects described herein, the physical form of the dosage form and the physical properties thereof can be tailored accordingly. The dosage forms can be a capsule, a tablet, or a gel cap. The structure or formats of the dosage form, the release of the minocycline, the physical construction of the dosage forms, and the ingredients thereof and therein will result in the dosage form reaching the target area(s) and having the desired temporal properties. The dosage forms can assume structures or formats that provide a variety of different physicochemical profiles or properties. As stated earlier, the dosage forms can be floatable, swellable, bioadhesive, osmotic, or any combination thereof. The minocycline release from the dosage form can be osmotically regulated either alone or in combination with one or more of the three immediately above noted dosage forms.

A variety of suitable dosage forms for use in this disclosure are well-known in the art, and can be prepared using conventional components. The following description of certain preferred dosage forms is intended to be illustrative of the invention. The dosage forms of this disclosure include dosage forms that combine certain desirable properties, such as any combination of floatable, swellable, bioadhesive, and osmotic.

Floatable Dosage Forms

A floating dosage form is a dosage form that substantially floats at the top surface or in proximity to the top surface of the gastric fluid in the stomach or upper gastrointestinal tract. Floating allows the dosage form to stay in the stomach or upper gastrointestinal tract longer than without floating. Floatable dosage forms typically contain a water-swellable polymer or gel-forming hydrocolloid therein that expands upon contact with the aqueous gastric fluid, thereby reducing the density of the dosage form and creating a buoyancy effect. Gas entrapped in pockets within the matrix of the swelled polymer or gel-forming hydrocolloid can also provides a buoyancy effect. Organic or inorganic excipients can also be included in the floatable dosage form. For example, certain excipients can reduce the density of the dosage form leading to floatability.

According to an embodiment of the present disclosure, the floating dosage form has an amount of minocycline, an amount of a water-swellable polymer or a gel-forming hydrocolloid, and an amount of an effervescent or gas-generating agent that can generate carbon dioxide (or other gas) upon contact with an acidic aqueous medium. The water-swellable polymer or gel-forming hydrocolloid is capable of retaining at least a portion of the gas generated upon contact with the acidic aqueous medium and thereby controls the spatial localization of the dosage form by causing it to float on or near the surface of the acidic gastric medium. This localization facilitates the subsequent delivery of the minocycline into the stomach and/or small intestine. The water-swellable polymer or gel-forming hydrocolloid can further control the temporal release of the minocycline from the dosage form. Useful effervescent or gas-generating agents include, for example, sodium bicarbonate in combination with citric acid or tartaric acid. In another embodiment, an organic excipient can be used in place of or in addition to the effervescent or gas-generating agent to achieve a dosage form lower in density compared to the aqueous gastric medium rendering it floatable.

In another embodiment, the floatable oral dosage form has an amount of minocycline, an amount of a water-swellable polymer or a gel-forming hydrocolloid, and an amount of an organic excipient. The organic excipient reduces the density of the dosage form causing it to float on or near the surface of the acidic medium.

The floating dosage form can be a non-biphasic extended release form using a floating mechanism other than organic excipients, such as gas-generating agents or microporous beads.

In accordance with the present disclosure, there is provided a method of treating acne in a human patient by administering any one of the floatable oral dosage forms to the patient once per day.

In particular embodiments, the dosage form is both floatable and bioadhesive, as described herein. In a further embodiment, the dosage form is floatable, swellable and bioadhesive.

The floatable dosage form can also be used in conjunction with an osmotic dosage release. The osmotic controlled or regulated release dosage form uses salt content in its interior to create an osmotic gradient with respect to the gastric juice or intestinal fluid to induce or drive liquid infiltration therein that results in the release of the minocycline at a constant rate.

Swellable Dosage Forms

A swellable dosage form is a dosage form that swells upon contact with gastric juice and expands to assume a volume larger than the original volume. Swelling makes the dosage form too large to readily pass through the pyloric sphincter between the stomach and duodenum and allows the dosage form to stay in the stomach longer than without swelling. Swelling typically occurs when a water-swellable polymer within the dosage form expands upon contact with the aqueous gastric fluid. In a particular embodiment, a swellable dosage form may swell to several times its original (non-swelled) volume. A preferred dosage form will retain mechanical rigidity after swelling sufficient to enable it to withstand peristalsis and mechanical contraction of the stomach.

According to an embodiment of the present disclosure, the swellable dosage form can be an oral dosage form in the form of a tablet that has a first layer and a second layer. The first layer includes an amount of one or more polymers or other excipients that are water-swellable and bioadhesive. The second layer includes an amount of minocycline and an amount of one or more polymers or other excipients that controls the spatial delivery and/or temporal release of the minocycline in an aqueous media in the stomach and/or small intestine.

In another embodiment, the swellable dosage form can be an oral dosage form that has an amount of minocycline and an amount of one or more water-swellable polymers or other excipients. The one or more water-swellable polymers control the spatial delivery and/or temporal release of the minocycline in an aqueous media in a targeted area of gastrointestinal tract of a patient, particularly the stomach and/or small intestine.

In yet another embodiment, the swellable dosage form can be an oral dosage form that has a therapeutic amount of minocycline and a swellable carrier system that renders the dosage form swellable upon contact with gastric fluid. In another embodiment, the dosage form is swellable for at least about three hours.

The swellable dosage form can be an extended release dosage form exhibiting a wide range of rates and extents of expansion or swelling. A swellable dosage form can swell to several times or more of its original (non-swelled) volume, e.g., up to 2 times, 4 times, 8 times, and 12 times. The swellable extended release dosage form can be in unitary phase. The swellable extended release dosage form can be with monophasic release.

In accordance with an embodiment of the present disclosure, there is provided a method of treating acne in a human patient by administering any one of the swellable oral dosage forms to the patient once per day.

In certain embodiments, the swellable dosage form can also be floatable or buoyant. In certain embodiments, the swellable dosage form can also be bioadhesive. In another embodiments, the swellable dosage form can be bioadhesive and floatable. In still other embodiments, the swellable dosage form can also be osmotic.

Bioadhesive Dosage Forms

A bioadhesive dosage form is a dosage form that can adhere to the inner or epithelial wall of the stomach or the small intestine, particularly that of the stomach due to the high incidence of mucus there. Mucus is a hydrated, viscous anionic hydrogel layer protecting the gastric mucosa. Mucus has therein mucin, which is composed of flexible cross-linked glycoprotein polymers. The dosage form can contain one or more bioadhesive polymers that have chains that can intertwine with the chains of the glycoprotein polymers of the mucin. The intertwining of chains creates an adhesion effect. Adhesion increases the retention or residence time of the dosage form in the stomach or small intestine. The retention or residence time of the dosage form is, however, inherently limited by the continuous biological turnover of gastric mucus, which diminishes adhesion of the dosage form to the inner or epithelial wall of the stomach over time.

The dosage form can contain one or more polymers that contain mucus or site-specific ligands that have affinity for, e.g., mucus or the inner epithelial wall of the stomach or small intestine. The ligands can be covalently bonded to a polymer, and suitable ligands include, for example, tetrafunctional anions, such as sodium tetraborate, salts of divalent cations, such as calcium or magnesium chloride, and polycationic agents, such as polylysine, polyarginine or polymyxin B, and pharmaceutically acceptable salts thereof.

According to an embodiment of the present disclosure, the bioadhesive oral dosage form has an amount of minocycline and an amount of a bioadhesive polymer that enables the dosage form to adhere to the inner or epithelial wall of the gastrointestinal tract. The bioadhesive polymer controls the spatial delivery and/or temporal release or delivery of the minocycline in an aqueous media in a targeted area of gastrointestinal tract of a patient, most particularly the stomach and/or small intestine. The dosage form optionally further includes a release controlling polymer which may also assist in controlling the spatial delivery and/or temporal release of the minocycline, and a binder.

In another embodiment, the bioadhesive oral dosage form has an amount of minocycline and an amount of one or more bioadhesive polymers. The one or more bioadhesive polymers enable the dosage form to adhere to the inner or epithelial wall of the stomach and/or the small intestine. The one or more bioadhesive polymers controls the spatial delivery and/or temporal release of the minocycline in an aqueous media in a targeted area of gastrointestinal tract of a patient, most particularly the stomach and/or the small intestine.

In accordance with the present disclosure, there is provided a method of treating acne in a human by administering any one of the bioadhesive oral dosage forms to the patient once per day.

In certain embodiments, the bioadhesive dosage form can also be floatable or buoyant. In other embodiments, the bioadhesive dosage form can also be a swellable dosage form. In still other embodiments, the bioadhesive dosage form can be combined with an osmotic dosage form.

Osmotic Dosage Forms

An osmotic dosage form is a dosage form that uses salt content in its interior to create an osmotic gradient with respect to the gastric juice or intestinal fluid to induce or drive liquid infiltration therein at a rate higher than the rate without the osmotic gradient. The osmotic gradient is counteracted by infiltration-regulating polymers, e.g., HPMC or carbomer, within the dosage form. The salt used to establish the osmotic gradient can be, for example, a pharmaceutically acceptable salt of minocycline, such as, but not limited to, minocycline hydrochloride or minocycline succinate. Sodium chloride or another inactive pharmaceutically acceptable salt can also be used to establish the gradient.

Again, it is possible for the oral dosage form to exhibit two or more of the physical properties described for the aforementioned dosage form types. For instance, a dosage form can be bioadhesive and swellable or bioadhesive and floatable. For instance, a dosage form can be floatable and swellable. For instance, the dosage form can be swellable and osmotic or floatable and osmotic.

In certain embodiments, additional extended release, and possibly delayed release or pulsatile release dosage forms can be used that do not necessarily exhibit the above-described physical properties to a significant degree. In other words, they release minocycline in designed profiles without floating or undergoing significant swelling or exhibiting adhesion to the inner stomach or duodenal wall. However, such dosage forms are less preferred.

Release Profiles

Generally, the dosage form can have an immediate, delayed, extended, sustained, pulsatile or any combination of these release profiles. In some embodiments, there is an immediate release but it is in combination with one or more of the other releases.

The present disclosure provides for modified release profiles that are believed to be more therapeutically effective per amount of minocycline administered to a patient than prior release profiles. A preferred modified release profile has an immediate release component and a delayed release component. The modified release profile regulates the commencement time and duration of the release of the minocycline into the gastrointestinal tract of the patient. The modified release profile also regulates the site of release of the minocycline into the gastrointestinal tract.

The modified release profile is a release selected from the group consisting of delayed; combined immediate and delayed; combined immediate, delayed and prolonged. The modified release profile further is optionally inclusive of a pulsatile release component. The modified release profile is further optionally inclusive an osmotically controlled release component.

As used herein:

(A) "Delayed Release" (DR) means release of the minocycline is delayed until sometime after initial administration. An example of delayed release is passing through the stomach and releasing in the duodenum. For example, a delayed release formulation can start to release minocycline into the gastrointestinal tract of the user after at least about 5 hours, after at least about 4.5 hours, after at least about 4 hours, after at least about 3.5 hours, after at least about 3 hours, or after at least about 2.75 hours, or after at least about 2.5 hours, or after at least about 2.25 hours, or after at least about 2 hours, or after at least about 1.75 hours, or after at least about 1.5 hour, or after at least about 1.25 hours, or after at least about, or after at least about 0.75 hour, or after at least about 0.5 hour, or after at least about 0.4 hour, or after at least about 0.3 hour, or after at least about 0.2 hour, or after at least about 0.1 hour from ingestion.

(B) "Extended Release" (ER) means the minocycline is released in a slow, continuous manner over an extended period of time upon administration of the dosage form to the patient. The extended release can commence immediately or some time later. Expressions such as "prolonged-action" and "sustained-release" have also been used to describe such dosage forms. For example, extended release formulation can release minocycline into the gastrointestinal tract of the of the user for a period of at least about 48 hours, or at least about 36 hours, or at least about 24 hours, or at least about 18 hours, or at least about 12 hours, or at least about 10 hours, or at least about 8 hours, or at least about 6 hours, or at least about 5 hours, or at least about 4 hours, or at least about 3 hours, or after at least about 2.5 hours, or after at least about 2 hours, or at least about 1.5 hour from ingestion.

(C) "Immediate Release" (IR) means release of minocycline takes place immediately upon administration of the dosage form to the patient or within a relatively brief period of time thereafter. For example, an immediate release formulation can release at least 80%, or at least 85%, or at least 90%, or at least 95%, or at least 99% of minocycline into the gastrointestinal tract of the user within a period of less than about 2 hours, or less than about 1.75 hour, or less than about 1.5 hour, or less than about 1.25 hour, or less than about 1 hour, or less than about 0.75 hour, or less than about 0.5 hour, or less than about 0.4 hour, or less than about 0.3 hour, or less than about 0.2 hour, or less than about 0.1 hour from ingestion.

(D) "Pulsatile Release" (PR) means release takes place in a pulse or burst profile and can take place initially upon administration of the dosage form to the patient and/or later or repeatedly after administration. For example, a pulsatile release formulation can release a burst of minocycline into the gastrointestinal tract of the user about every 0.1 hour, or about every 0.2 hour, or about every 0.3 hour, or about every 0.4 hour, or about every 0.5 hour, or about every 0.6 hour, or about every 0.7 hour, or about every 0.8 hour, or about every 0.9 hour, or about every 1 hour, or about every 1.25 hour, or about every 1.5 hour, or about every 1.75 hour, or about every 2 hour2, or about every 2.5 hours, or about every 3 hours, or about every 3.5 hours, or about every 4 hours, or about every 4.5 hours, or about every 5 hours, or about every 5.5 hours, or about every 6 hours, or about every 6.5 hours, or about every 7 hours, or about every 7.5 hours, or about every 8 hours.

(E) "Controlled Release (CR) means any regulation of release of minocycline and can include immediate release, extended release, delayed release, pulsatile release, and combinations thereof.

The delivery of the minocycline can be metered. Also, the delivery can be targeted to commence release in a specific area or location of the patient and for a period of time after administration and maintain release for as long as possible in the specific location. Thus, the release profile of the present disclosure can have a metered, steady release as part of its modified release profile. As used herein, metered, steady release profile means a release profile controlled in the amount released at any given time over a given period of time. Preferably, the metered, steady release is a constant release.

The dosage form can be formulated to have extended-release profiles for minocycline of desired duration. For instance, a 2.5-hour release profile in simulated gastric fluid (SGF) can have a release of about 35% to about 60% in 1 hour and at least about 90% in 2.5 hours; a 4-hour release profile can have a release of about 5% to about 65% dissolution at 1 hour and at least 75% at 4 hours; a 4-hour release profile can have a release of about 35% to about 50% in 1 hour, about 60% to about 75% in 2 hours, and at least about 90% in 4 hours; and a 5-hour release profile can have a release of about 25% to about 40% in 1 hour, about 50% to about 70% in 3 hours, and at least about 90% in 5 hours. Release can be formulated to occur in the stomach and/or the small intestine as desired. The dosage forms can be designed to be retained in the stomach for the entire release profile, e.g., swellable, yet release the minocycline to the duodenum during this release phase.

The dissolution profile of embodiments of dosage forms and delivery systems of the present disclosure can be measured using, as is known, simulated gastrointestinal tract (SIG) techniques. SIG as used herein means as measured in a device that provides a simulated gastric fluid (SGF) that is 750 mL diluted HCl pH 1.1 using USP dissolution apparatus 2 (paddle) at a speed of 75 RPM and a temperature of 37° C., and/or simulated intestinal fluid (SIF) that is 750 mL diluted HCl pH 1.1+200 mL phosphate buffer pH 6 using USP dissolution apparatus 2 (paddle) at a speed of 75 RPM and a temperature of 37° C. The buffer is 0.1 N NaOH in 200 mM phosphate buffer adjusted to pH 6.0 using 2 N HCl and/or 2N NaOH.

Excipients

In embodiments of dosage forms of the present disclosure, the release of minocycline can also be controlled or regulated by the use of excipients. Excipients can perform functions other than control or regulate the release of minocycline. Excipients include, but are not limited to one or more disintegrants, wetting agents, diluents, carriers or vehicles (solid, semi-solid, or liquid), glidants, colorants, binders, lubricants, release regulating agents, pH adjusting agents, water-swellable polymers, gel-forming hydrocolloids, effervescent or gas-generating agents, organic materials, and osmotic agents. A particular excipient may serve multiple functions. Excipients that are generally characterized as falling within one or more of the above categories are well know-in the art, and suitable examples of such excipients are provided herein. The dosage forms described herein can be formulated with any one, or any combination of suitable excipients.

Useful excipients that can control or regulate the release of minocycline from the dosage form of the present disclosure can be polymeric or non-polymeric, organic or inorganic, water-soluble or non-water soluble, or in the form of a solid, semi-solid, or liquid. Useful organic excipients include one or more fatty acids and esters thereof, fatty alcohols, lipid waxes, amphiphilic waxes, and gums. Examples of fatty acids and esters thereof include glyceryl monostearate, glyceryl monooleate, lauric acid, and stearic acid. Examples of fatty alcohols include stearyl alcohol, cetostearyl alcohol, cetyl alcohol, and myristyl alcohol. Examples of gums include acacia, gelatin, tragacanth, veegum, xanthan and chitosan. Examples of waxes include beeswax, carnauba wax, spermaceti wax, candelilla wax, cocoa butter, and paraffin. Other useful organic excipients include polymeric glycols, such as polyethylene glycol and propylene glycol. A useful polymeric glycol is, for example, PEG-6000.

Useful polymeric excipients include, for example, methyl cellulose (MC), carboxymethylcellulose (CMC), ethyl cellulose (EC), hydroxyethyl cellulose (HEC), hydroxypropyl cellulose (HPC), hydroxypropyl methylcellulose (HPMC), and any combinations thereof.

Useful disintegrants include, for example, cornstarch, pregelatinized starch, cross-linked carboxymethyl cellulose sodium, sodium starch glycolate, and polyvinylpolypyrrolidone (PVP). Other useful disintegrants include croscarmellose sodium, crospovidone, starch, alginic acid, sodium alginate, clays (e.g. veegum or xanthan gum), cellulose floc, ion exchange resins, or effervescent systems, such as those utilizing food acids (such as citric acid, tartaric acid, malic acid, fumaric acid, lactic acid, adipic acid, ascorbic acid, aspartic acid, erythorbic acid, glutamic acid, and succinic acid) and an alkaline carbonate component (such as sodium bicarbonate, calcium carbonate, magnesium carbonate, potassium carbonate, ammonium carbonate, etc.).

Examples of useful glidants include silicon dioxide, colloidal silicon dioxide, magnesium trisilicate, powdered cellulose, starch, talc, and tribasic calcium phosphate.

Examples of useful lubricants include stearic acid, magnesium stearate, calcium stearate, talc, and zinc stearate. Examples of useful wetting agents include sodium lauryl sulfate, poloxamer, and docusate sodium. Useful diluents or fillers include, for example, lactose, calcium carbonate, calcium phosphate, dibasic calcium sulfate, tribasic calcium phosphate, microcrystalline cellulose, dextran, starch, pregelatinized starch, sucrose, xylitol, lactitol, mannitol, sorbitol, sodium chloride, and polyethylene glycol.

Useful binders include, for example, methylcellulose, hydroxyethyl cellulose, hydroxypropyl cellulose, hydroxypropyl methylcellulose, polyvinylpyrrolidone (PVP), and polyvinylpyrrolidone/vinyl acetate copolymer. Other commonly used binders include cellulosic polymers such as carboxymethyl cellulose; microcrystalline cellulose; starch; sugars such as sucrose, glucose, dextrose, lactose; and gums such as guar gum and tragacanth gum.

Swellable polymers useful in the dosage forms include, but are not limited to, methylcellulose, ethyl cellulose, hydroxypropyl cellulose, carboxymethylcellulose sodium, hydroxypropyl methylcellulose, polycarbonate polymers, polyvinyl acetate, agar, carbomer, polycarbophil, polyethylene oxide, chitosan, and alginate. Among the bioadhesive polymers are carbomer, chitosan, polycarbophil, and polyvinylpyrrolidone. Polycarbophil, a polyacrylic acid cross-linked with polyalkenyl ethers or divinyl-glycol, is a preferred bioadhesive polymer or excipient. A preferred class of polycarbophils is Noveon® polycarbophils, as an example Noveon®-AA1. Noveon® polycarbophils may swell in water up to 1000 times their original volume (and up to ten times their original diameter).

The amount of excipient(s), including swellable and bioadhesive polymers, employed in the dosage form will vary and depend on a number of factors, such as properties of the excipient(s), properties of the minocycline active, desired minocycline release profiles, configuration of the dosage form, the process for making the dosage form, the modality of the dosage form, and the mode of administration of the dosage form.

Suitable gas-generating agents can be any compound or compounds that produce effervescence, such as a solid acid compound and a solid basic compound that, in the presence of a fluid, can react to form a gas, such as carbon dioxide. Examples of acid compounds include, organic acids such as malic, fumaric, tartaric, itaconic, maleic, citric, adipic, succinic and mesaconic, and inorganic acids such as sulfamic or phosphoric, also acid salts such as monosodium citrate, potassium acid tartrate and potassium bitartrate. Examples of basic compounds include, for example, metal carbonates and bicarbonates salts, such as alkali metal carbonates and bicarbonates.

In some embodiments, a dosage form may be coated with an enteric coating material(s) or have such a coating over a component within the dosage form. An enteric coating material can include a coating polymer(s) (or non-polymer(s)) and/or other excipients that are substantially insoluble in the acidic environment of the stomach but is substantially soluble in duodenal/intestinal fluids at certain pH levels, typically in a pH range of about 5 to about 7, more particularly a pH of about 5.5 to about 6.5. The enteric coating material may include a non-toxic, pharmaceutically acceptable polymer, for example, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, polymeric methacrylates, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resin such as zein, shellac and copal collophorium, and commercially available enteric dispersion systems (e.g., EUDRAGIT® L30D55, EUDRAGIT® FS30D, EUDRAGIT® L100, KOLLICOAT® EMM30D, ESTACRYL® 30D, Acryl-EZE®, COATERIC®, and AQUATERIC®). The enteric coating may also include one or more plasticizers, such as acetyltriethyl citrate, triethyl citrate, acetyltributyl citrate, dibutylsebacate, triacetin, polyethylene glycol, and propylene glycol. The coating may also have an anti-tacking agent such as talc.

The enteric coating material will typically be applied at about 1 wt % to about 50 wt % and more typically about 4 wt % to about 25 wt % based on the combined weight of the coating and the remainder of the dosage form. Dosage forms may be coated by any method known in the art, including coating with aqueous-based solutions or dispersions, or organic-based solutions or dispersions, in which polymer-containing droplets are atomized with air and sprayed onto the substrates (pan coating or fluid bed coating) or applied electrostatically. When formulated with an enteric coating, a dosage form can have a delayed release of at least about 90 wt % of minocycline within about 2 hours to about 5 hours after arrival in the duodenum, e.g., release of at least about 90 wt % of minocycline within about 2 hours to about 5 hours at a pH of 6.5.

The dosage form can take the form of any known in the art, such as a tablet, a capsule, a caplet, a gel cap, and a microparticulate. Capsules can be hard-shell or soft-shell. Capsules can be formed of any natural or synthetic water-soluble polymer, such as HPMC or gelatin.

In all embodiments, the dosage forms contemplated range from about 10 mg to about 135 mg of minocycline based on minocycline free base equivalent weight. Particular dosage forms include those of 35 mg, 60 mg, 85 mg and 110 mg. Other dosage forms include, e.g., 15 mg, 20 mg, 25 mg, 30 mg, 35 mg, 40 mg, 45 mg, 50 mg, 55 mg, 65 mg, 70 mg, 75 mg, 80 mg, 90 mg, 95 mg, 100 mg, 105 mg, 110 mg, 115 mg, 120 mg, 125 mg, 130 mg, 140 mg, 150 mg, 160 mg, 170 mg, 190 mg, or 200 mg.

Tablet, Capsule, and Caplet Dosage Forms

In some embodiments, the oral dosage form is a tablet or capsule that comprises a therapeutically effective amount of minocycline, and a specialized polymer, such as a polymer of acrylic acid cross-linked with polyalkenyl ethers or divinyl chloride. The specialized polymer is a dual-purpose polymer capable of enhancing bioadhesion and prolonging, in a controlled fashion, the minocycline release to create a more constant ADME/PK profile for the minocycline. In a species of this embodiment, the polymer is a polycarbophil cross-linked with polyalkenyl ethers or divinyl glycol. The bioadhesive properties increase residence time in the stomach, and the controlled release properties increase the maximum plasma concentration (CMAX) and maintain a long sustained area under the curve (AUC), which reduces the variability of antibiotic release and allows for a uniform release over time with minimal/no peaks or spikes. The bioadhesive and controlled release properties assist with targeted delivery of the minocycline to the duodenum for possible maximum absorption.

Polymers of acrylic acid useful in this dosage form include a mix of suitable bioadhesive carbomers or polycarbophils, more preferably a polycarbophil, which is a polyacrylic cross-linked with polyalkenyl ethers or divinylglycol, and most preferably where the polycarbophil is the Noveon® AA-1 polycarbophil. Noveon® polycarbophils are polymers of acrylic acid, crosslinked with polyalkenyl ethers or divinyl glycol. These polymers swell in water up to 1,000 times their original volume (and ten times their original diameter) to form gels when neutralized.

Additional polymers useful in this dosage form include multiple polymers (sodium alginates, CMC, polyoxyethylene-polyoxypropylene) and biodegradable polymers such as PLGA and PLA. Examples of biodegradable polymers include: (i) polyhydroxy butyrate (PHB); (ii) poly-hydroxybutyrate-co-b-hydroxy valerate (PHBV); (iii) polyglycolic acid (PGA); (iv) polylactic acid (PLA); and (v) poly (I-caprolactone) (PCL).

In a further embodiment, the dosage forms comprise a tablet that has a first layer and a second layer. The first layer includes an amount of one or more polymers capable of adhering to at least a portion of the inner wall of the stomach and/or duodenum. The second layer includes an amount of minocycline and an amount of one or more polymers that controls the delivery of the minocycline. The one or more polymers capable of adhering to at least a portion of the inner wall of the stomach and/or duodenum can include a carbomer. The one or more polymers can include hydroxypropylmethylcellulose. Microcrystalline cellulose can be in each of the first and second layers. Also, an amount of mannitol can be in the layer that includes minocycline.

In still another embodiment, the oral dosage form is preferably a tablet that has an extended-release oral dosage form, having an amount of minocycline, an amount of carbomer, and an amount of polycarbophil. The dosage form can further include polyvinyl pyrrolidone. The minocycline in one embodiment of this oral dosage form has a dissolution profile in aqueous media, for example in SGF or SIG, of about 30% to about 50% in 4 hours, about 60% to about 75% in 8 hours, and at least about 90% in 12 hours. In another embodiment, the minocycline in the oral dosage form has a dissolution profile in aqueous media, for example in SGF or SIG, of about 20% to about 40% in 8 hours, about 50% to about 70% in 16 hours, and at least about 80% in 24 hours.

In a further embodiment, the dosage form is preferably a tablet that has an extended-release oral dosage form, having an amount of minocycline, an amount of carbomer, an amount of polycarbophil, and sodium bicarbonate. The carbomer and the polycarbophil control the spatial and temporal delivery of the minocycline in an aqueous media in the duodenum, the targeted area of gastroretentive tract of the patient. In one species of this embodiment, the dosage form is floatable and bioadhesive. The minocycline has a dissolution profile in aqueous media, for example in SGF or SIG, of about 35% to about 60% in 1 hour and at least about 90% in 2.5 hours. In another species of this embodiment, the minocycline has a dissolution profile in aqueous media, for example in SGF or SIG, of about 25% to about 40% in 1 hour, about 50% to about 70% in 3 hours, and at least about 90% in 5 hours. The release is about 2.5 hours and 5 hours in the duodenum.

In another species of this embodiment, this extended release oral dosage form is targeted for the stomach. The dosage form can be bioadhesive and floatable, and can have a release of between 2.5 hour and 5 hour in the stomach. The minocycline in the oral dosage form has a dissolution in aqueous media, for example in SGF or SIG, of about 35% to about 60% in 1 hour and at least about 90% in 2.5 hours and, in another aspect, of about 25% to about 40% in 1 hour, about 50% to about 70% in 3 hours, and at least about 90% in 5 hours.

In a still further embodiment, the dosage form is an extended release tablet having an amount of minocycline, and an amount of a water-swellable polymer other than pregelatinized starch. The water swellable polymer other than pregelatinized starch controls the spatial and temporal delivery of the minocycline. The minocycline can have a dissolution profile in aqueous media, for example in SGF or SIG, of about 35% to about 50% in 1 hour, about 60% to about 75% in 2 hours, and at least about 90% in 4 hours. The dosage tablet can also have an anionic polymer selected from the group consisting of cross-linked acrylic acid polymer, methacrylic acid polymer, alginate, and carboxymethyl cellulose.

In a yet further embodiment, the dosage form is a prolonged release bioadhesive tablet having a polymer of acrylic acid, cross-linked with polyalkenyl ethers or divinyl glycol, and a therapeutically effective amount of minocycline.

In another embodiment, the oral dosage form is a tablet or capsule that has a pulsatile dosage form having a solid dispersion that includes an amount of minocycline, one or more organic carriers, one or more diluents, and one or more bioadhesive polymers. In this embodiment, the targeted area is the duodenum. The one or more organic carriers are lauric acid, PEG-6000, cetostearyl alcohol, or any combinations thereof. The one or more diluents are mannitol. The one or more bioadhesive polymers are hydroxypropylcellulose.

In a further embodiment, the oral dosage form is a pulsatile oral dosage form is a capsule or tablet that has a solid dispersion that includes an amount of minocycline, one or more diluents, and one or more bioadhesive polymers. The targeted area is the duodenum. The one or more diluents are mannitol. The one or more bioadhesive polymers are polycarbophil.

In a still further embodiment, the oral dosage form is a tablet or a capsule that has a solid dispersion of an amount of minocycline, an amount of one or more water soluble polymers; and an amount of one or more organic carriers. The dosage form has a plurality of nanoparticles. The targeted area is the duodenum. The one or more water soluble polymers are chitosan. The one or more organic carriers are glycerol monooleate.

In a yet further embodiment, the oral dosage form is an extended release tablet or capsule that has an amount of minocycline, an amount of one or more pH insensitive controlled release polymers, and an amount of one or diluents. The targeted area is the stomach, duodenum, or a combination thereof. In another embodiment, the oral dosage form has an extended release tablet or capsule that has an amount of minocycline, an amount of one or more controlled release polymers, a buffer, and an amount of one or diluents.

In other embodiments of dosage forms of the present disclosure, the release of minocycline can be controlled by the use of excipients such as organic carriers and diluents. Useful organic carriers include glyceryl monostearate, lauric acid, PEG-6000, and cetostearyl alcohol. Useful diluents include lactose monohydrate and mannitol. In still other embodiments of dosage forms of the present disclosure, the release of minocycline can be controlled in both the stomach and duodenum by the use of pH-insensitive controlled-release polymers. In yet other embodiments in which pH-sensitive controlled release polymers are used, buffers may be employed to mediate pH effects on release rates. To prolong gastric residence time, gas-generating excipients, such as carbomer, cellulosic polymers, and chitosan, may be employed. N-acetyl cysteine may, if desired, be incorporated into some formulations as an antioxidant. N-acetyl cysteine is readily absorbed and non-toxic. A useful amount is 50 mg of N-acetyl-cysteine per unit capsule. In all embodiments, the dosage forms contemplated range from about 60 mg to about 180 mg of minocycline based on minocycline base equivalent weight. Particular dosage forms include those of 60 mg, 120 mg, and 180 mg. Other dosage forms include, e.g., 10 mg, 15 mg, 20 mg, 25 mg, 30 mg, 35 mg, 40 mg, 45 mg, 50 mg, 55 mg, 65 mg, 70 mg, 75 mg, 80 mg, 85 mg, 90 mg, 95 mg, 100 mg, 105 mg, 110 mg, 115 mg, 125 mg, 130 mg, 140 mg, 150 mg, 160 mg, 170 mg, 190 mg, or 200 mg of minocycline.

In another embodiment, the present disclosure includes a method of assisting a physician in prescribing a dose of minocycline for the treatment of acne. The method includes determining the body weight of a patient, referring to a chart or reference tool that correlates a plurality of body weight ranges with a corresponding number of dosage forms each having a different level of minocycline based on a target dosage and identifying a single dosage form corresponding to a particular weight range in which the patient's weight falls in the chart or reference tool. The method can include administering to the patient the identified single dosage form.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the present disclosure.

What is claimed is:

1. A method for treating acne in a patient comprising:
   administering to said patient an oral dosage form comprising minocycline wherein the dosage form comprises an immediate release component and a delayed release component;
   controlling the spatial and temporal delivery of the minocycline administered in the delayed release component of the oral dosage form into a gastrointestinal area of the patient selected from the group consisting of the stomach, the duodenum of the small intestine, and a combination thereof;
   wherein the delayed release component of the oral dosage form has a modified release profile and/or a physicochemical profile selected from the group consisting of floatable, swellable, bioadhesive, osmotic, and any combination thereof;
   wherein the delayed release component of the oral dosage form regulates the release of minocycline into the gastrointestinal area of the patient such that the oral dosage form exhibits $T_{max}$ and $C_{max}$ so that vestibular and/or gastrointestinal side effects are minimized or eliminated, while reducing the acne in the patient;
   wherein the controlled temporal release in the gastrointestinal area of the patient is completed in about 2.5 hours to about 7.0 hours after administration to the patient; and
   wherein the oral dosage form has a bioavailability of minocycline of 50% or greater relative to an immediate release dosage form.

2. The method of claim 1, wherein the oral dosage form has a reduced amount of minocycline that would otherwise need to be delivered to the patient to achieve the given reduction of acne.

3. The method of claim 1, wherein the bioavailability of minocycline is 85% or greater relative to immediate release minocycline.

4. The method of claim 1, wherein the release of minocycline is substantially entirely in the stomach or substantially entirely in the duodenum.

5. The method of claim 1, wherein the release of minocycline is in both the stomach and the duodenum and the release of minocycline in the duodenum commences within about 2 hours after arrival of the oral dosage form in the duodenum.

6. The method of claim 1, wherein the minocycline is selected from the group consisting of minocycline base, minocycline maleate, minocycline mesylate, and minocycline hydrochloride.

7. The method of claim 1, wherein said oral dosage form has a floatable physicochemical profile comprising:
   a first component comprising: an amount of minocycline contained in enteric coated substantially spherical pellets;
   a second component comprising: an amount of a water-swellable polymer or a gel-forming hydrocolloid selected from the group consisting of a carbomer, an HPMC, a polycarbophil, and any combinations thereof and an amount of a gas-generating agent that generates carbon dioxide gas upon contact with an acidic aqueous media selected from the group consisting of sodium bicarbonate, citric acid, tartaric acid, and any combinations thereof;

wherein said water-swellable polymer or the gel-forming hydrocolloid is capable of retaining at least a portion of the carbon dioxide gas generated upon contact with the acidic aqueous media, wherein said water-swellable carbon dioxide retaining polymer causes said oral dosage form float and to swell so as to reside in a patient's stomach near the pyloric sphincter for between about 2 and about 5 hours, and wherein said enteric coating delays release of said minocycline until about at least one hour after ingestion of said dosage form and said enteric coating releases at least about 90% of said amount of minocycline within about 2 to about 5 hours after ingestion.

8. The method of claim 1 wherein said oral dosage form has a floatable physicochemical profile comprising:
   (a) an amount of minocycline and a floatable component, said floatable component selected from the group consisting of:
      (i) an amount of a water-swellable polymer or a gel-forming hydrocolloid capable of retaining at least a portion generated carbon dioxide gas and an amount of an agent that generates carbon dioxide gas upon contact with an acidic aqueous media;
      (ii) an amount of an effervescent agent that generates carbon dioxide gas upon contact with an acidic aqueous media and a carrier system is capable of retaining at least a portion of the carbon dioxide gas generated upon contact with the acidic aqueous media and rendering the dosage form floatable in the acidic aqueous media for at least three hours; and
      (iii) an amount of an organic excipient, wherein the dosage form floats on or near the surface of an acidic aqueous medium when contacted therewith.

9. The method of claim 1 wherein the delayed release component of said oral dosage form has a swellable physicochemical profile comprising:
   (a) an amount of minocycline and a swellable component, said swellable component selected from the group consisting of:
      (i) a swellable carrier comprising a first layer and a second layer, wherein the first layer includes an amount of one or more polymers or other excipients that are water-swellable and bioadhesive, wherein the second layer includes an amount of minocycline and an amount of one or more polymers or other excipients that controls the spatial delivery and/or temporal release of the minocycline in an aqueous media in the stomach and/or small intestine, wherein the dosage form is a tablet;
      (ii) an amount of one or more water-swellable polymers, wherein the one or more water-swellable polymers controls the temporal and/or spatial delivery of the minocycline in an aqueous media in a targeted area of gastrointestinal tract of a patient, wherein the targeted area is selected from the group consisting of the stomach, small intestine, and a combination thereof;
      (iii) a swellable carrier that renders the dosage form swellable for at least about three hours upon contact with simulated gastric fluid; and
      (iv) a swellable carrier that renders the dosage form swellable upon contact with simulated gastric fluid.

10. The method of claim 1 wherein said oral dosage form has a bioadhesive physicochemical profile comprising:
   (a) an amount of minocycline and a bioadhesive component, said bioadhesive component selected from the group consisting of:
      (i) an amount of one or more bioadhesive polymer(s), wherein the one or more bioadhesive polymer(s) controls the spatial delivery and/or temporal release of the minocycline in an aqueous media in a targeted area of gastrointestinal tract of a patient, wherein the targeted area is the stomach;
      (ii) an amount of one or more bioadhesive polymer(s), wherein the one or more bioadhesive polymer(s) controls the spatial delivery and/or temporal release of the minocycline in an aqueous media in a targeted area of gastrointestinal tract of a patient, wherein the targeted area is the small intestine;
      (iii) a carrier having bioadhesive properties, the bioadhesive properties providing that the dosage form will adhere to an inner wall of the stomach and reside in the stomach for about 3 to about 4 hours; and
      (iv) a carrier having bioadhesive properties, the bioadhesive properties providing that the dosage form will first adhere to an inner wall of the stomach and then adhere to the inner wall of the small intestine.

* * * * *